United States Patent [19]

Nohira et al.

[11] Patent Number: 4,904,410

[45] Date of Patent: Feb. 27, 1990

[54] MESOMORPHIC COMPOUND AND LIQUID CRYSTAL COMPOSITION CONTAINING SAME

[75] Inventors: Hiroyuki Nohira, Urawa; Masanao Kamei, Annaka; Shinichi Nakamura, Urawa; Takashi Iwaki, Atsugi; Kazuharu Katagiri, Tama; Yoko Yamada, Atsugi, all of Japan

[73] Assignee: Canon Kabushiki Kaisha, Tokyo, Japan

[21] Appl. No.: 174,384

[22] Filed: Mar. 28, 1988

[30] Foreign Application Priority Data

Mar. 31, 1987 [JP] Japan .................... 62-78001

[51] Int. Cl.$^4$ .............. G02F 1/13; C09K 19/34; C07D 239/02
[52] U.S. Cl. .............. 252/299.61; 252/299.01; 350/350 R; 350/350 S; 544/335
[58] Field of Search .............. 252/299.61, 299.01; 350/350 S, 350 R; 544/335

[56] References Cited

U.S. PATENT DOCUMENTS

| 4,725,688 | 2/1988 | Taguchi et al. | 252/299.61 |
| 4,834,904 | 5/1989 | Krause et al. | 252/299.61 |

FOREIGN PATENT DOCUMENTS

| 267585 | 5/1988 | European Pat. Off. | 252/299.61 |
| 293910 | 12/1988 | European Pat. Off. | 252/299.61 |
| 3515273 | 11/1986 | Fed. Rep. of Germany | 252/299.61 |
| 3515374 | 11/1986 | Fed. Rep. of Germany | 252/299.61 |
| 240385 | 10/1986 | German Democratic Rep. | 252/299.61 |
| 240386 | 10/1986 | German Democratic Rep. | 252/299.61 |
| 61-200972 | 8/1986 | Japan | 252/299.61 |
| 63-22042 | 1/1988 | Japan | 252/299.61 |
| 63-196571 | 8/1988 | Japan | 252/299.61 |
| 63-239275 | 10/1988 | Japan | 252/299.61 |
| 8705012 | 8/1987 | World Int. Prop. O. | 252/299.61 |
| 8705017 | 8/1987 | World Int. Prop. O. | 252/299.61 |
| 8705018 | 8/1987 | World Int. Prop. O. | 252/299.61 |

*Primary Examiner*—Teddy S. Gron
*Attorney, Agent, or Firm*—Fitzpatrick, Cella Harper & Scinto

[57] ABSTRACT

An optically active mesomorphic compound is represented by the following formula (I):

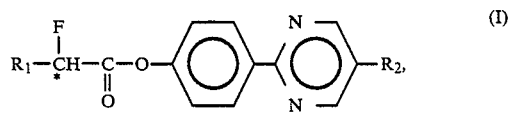

wherein $R_1$ and $R_2$ are respectively an alkyl group having 1 to 16 carbon atoms, and C* denotes an asymmetric carbon atom. The mesomorphic compound has a fluorine atom directly connected to the asymmetric carbon atom and is effectively used as a liquid crystal component providing an increased spontaneous polarization and an improved responsiveness.

21 Claims, No Drawings

MESOMORPHIC COMPOUND AND LIQUID CRYSTAL COMPOSITION CONTAINING SAME

FIELD OF THE INVENTION AND RELATED ART

The present invention relates to a novel mesomorphic compound, particularly an optically active mesomorphic compound, a liquid crystal composition containing such a mesomorphic compound, and a liquid crystal device using such a liquid crystal composition.

There is a well known type of liquid crystal device using TN (twisted nematic) type liquid crystals as shown, for example, in "Voltage-Dependent Optical Activity of a Twisted Nematic Liquid Crystal" by M Schadt and W. Helfrich, Applied Physics Letters, Vol. 18, No. 4 (Feb. 15, 1971), pp. 127–128. In this type of liquid crystal device, the number of picture elements have been restricted, because the phenomenon of problem that a crosstalk phenomenon occurs when a device of a matrix electrode structure with a high density of picture elements is driven according to a multiplexing driving scheme. Further, their use for display have been limited because of slow electric field response and poor visual angle characteristics.

Another type of liquid crystal device is known, one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the helical pitch thereof so that its helical structure is unwound to develop a bistability (e.g., U.S. Pat. No. 4,367,924).

As the bistable liquid crystal, a ferroelectric crystal showing a chiral smectic C phase (SmC*) or H phase (SmH*) is generally used.

Such a ferroelectric liquid crystal has very rapid response speed because of having spontaneous polarization. Also such crystals exhibit a memorizable bistable state and further have excellent vision angle characteristics and therefore are suitable for a display of large capacity and large picture area.

Further, since a material used as a ferroelectric liquid crystal has an asymmetry, it can be used as a functional material to be used in the following types of optical devices in addition to the use as a ferroelectric liquid crystal material:

(1) Those utilizing a cholesteric-nematic phase transition is a liquid crystal state (J. J. Wysoki, A. Adams and W. Haas: Phys. Rev. Lett., 20, 10204 (1968));

(2) Those utilizing a guest-host effect of the White-Taylor type in a liquid crystal state (D. L. White and G. N. Taylor: J. Appl. Phys. 45, 4718 (1974)).

These optical devices are important as display devices and modulation devices. The explanation of the individual system may be found in the respective references and is omitted here.

It is understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this view point, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives. However, it has been seldome to incorporate a polar group into such an intermediate. Partly for this reason, the above mentioned method of introducing a polar group directly to an asymmetric carbon atom has not ben utilized very effectively.

SUMMARY OF THE INVENTION

A principal object of the present invention is, in view of the above problems, to provide a mesomorphic compound having an enhanced electric fieldresponsive characteristic in a liquid crystal state by introducing a fluorine atom, which is stable and has a large dipole moment, directly to an asymmetric carbon atom.

Another object of the present invention is to provide a liquid crystal composition comprising at least one species of the mesomorphic compound.

A further object of the present invention is to provide a mesomorphic compound capable of readily changing the length of the alkyl chain and therefore capable of controlling a kind of liquid crystal phase to be developed in the liquid crystal state and a temperature range therefore as shown by H. Arnold: Z. Phys. Chem., 266, 146 (1964), and a liquid crystal composition containing at least one species of the mesomorphic compound.

According to the present invention, there is provided an optically active mesomorphic compound represented by the following formula (I):

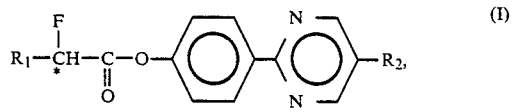

wherein $R_1$ and $R_2$ are respectively an alkyl group having 1 to 16 carbon atoms, and C* denotes an asymmetric carbon atom. Herein, the term "mesomorphic compound" is used to mean that the mesomorphic compound is not necessarily required to show a liquid crystal state by itself but it is sufficient that the mesomorphic compound is compatibly mixed with another mesomorphic compound to provide a liquid crystal composition showing a liquid crystal state.

According to the present invention, there are further provided a liquid crystal composition containing at least one species of the above mesomorphic compound as a constituent, and a liquid crystal device using the liquid crystal composition.

These and other objects, features and advantages of the present invention will become more apparent upon a consideration of the following description of the preferred embodiments of the present invention.

DETAILED DESCRIPTION OF THE PREFERRED EMBODIMENTS

The mesomorphic compound represented by the above formula (I) may be synthesized from an optically active intermediate such as a 2-fluoroalkanoic acid of the following formula (II):

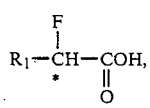
(II)

which in turn may be synthesized along the following scheme:

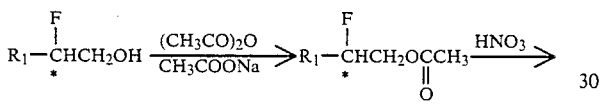

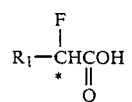

For example, the mesomorphic compound represented by the formula (I) may be produced from the 2-fluoroalkanoic acid along the following scheme:

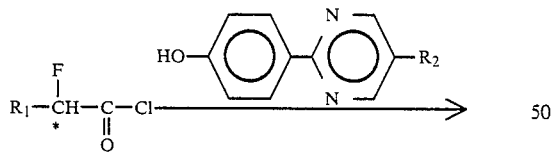

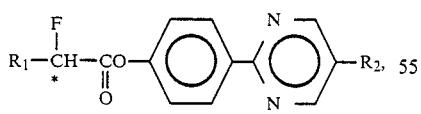

wherein $R_1$ and $R_2$ are the same as defined above.

The optically active mesomorphic compound according to the present invention represented by the formula (I) can have a wide variety of $R_1$ by changing the number of carbon atoms in the alkane moiety in the starting 2-fluoroalkanoic acid but those having an alkyl group $R_1$ of 1–16 are provided by the present invention.

Hereinbelow, specific examples of the mesomorphic compound (I) according to the present invention are enumerated hereinbelow:

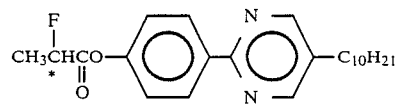
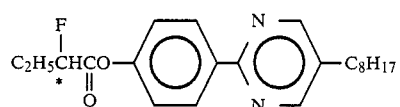
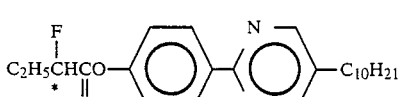
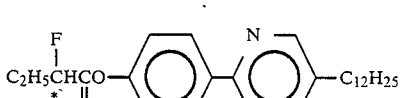
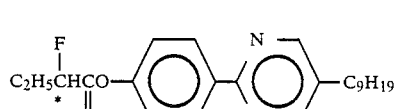
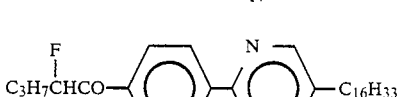
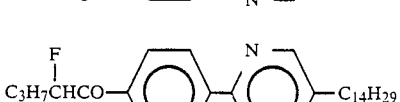
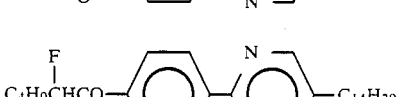
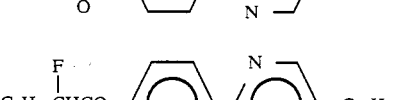
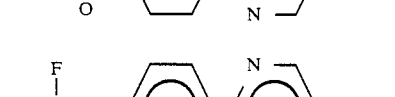

-continued

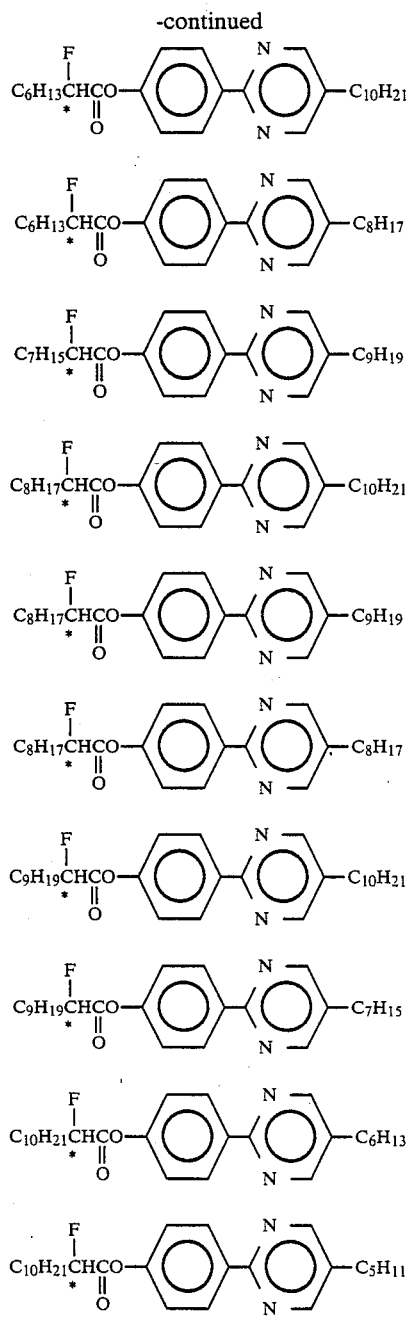

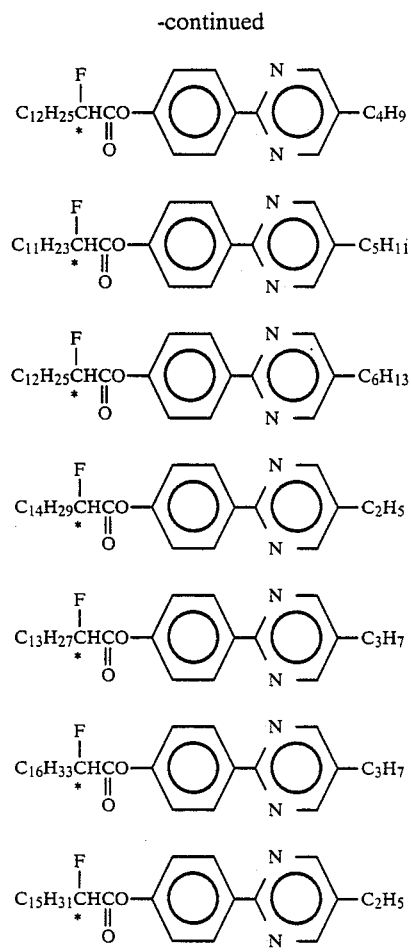

The liquid crystal composition according to the present invention contains at least one species of the mesomorphic compound represented by the formula (I). For example, the mesomorphic compound represented by the formula (I) may be mixed with a ferroelectric liquid crystal selected from those of the formulas <1>-<13> shown below to increase the spontaneous polarization and increase the response speed. In this case, it is preferred to use the mesomorphic compound represent by the formula (I) in an amount constituting 0.1-99 wt. %, particularly 1-90 wt. % of the resulting liquid crystal composition.

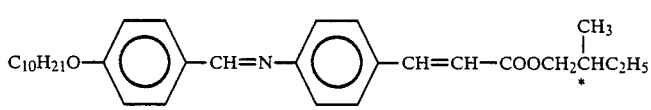

<1> p-decyloxybenzylidene-p'-amino-2-methylbutylcinnamate
(DOBAMBC)

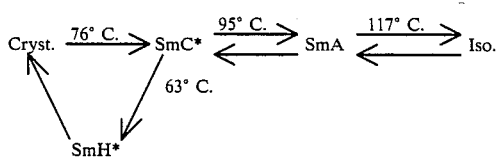

-continued

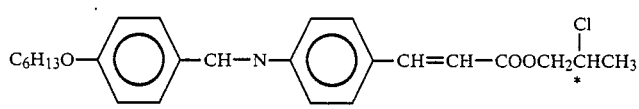

p-hexyloxybenzylidene-p'-amino-2-chloropropylcinnamate
(HOBACPC)

Cryst. $\underset{\longleftarrow}{\overset{60° C.}{\longrightarrow}}$ SmH* $\underset{\longleftarrow}{\overset{64° C.}{\longrightarrow}}$ SmC* $\underset{\longleftarrow}{\overset{78° C.}{\longrightarrow}}$ SmA $\underset{\longleftarrow}{\longrightarrow}$ Iso.

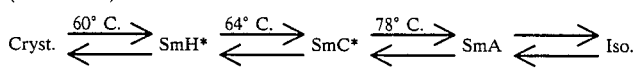

p-decyloxybenzylidene-p'-amino-2-methylbutyl-α-cyanocinnamate
(DOBAMBCC)

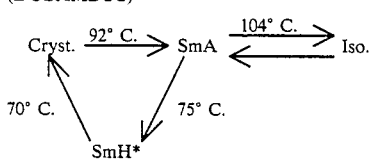

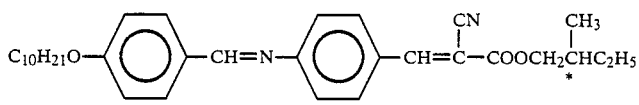

p-tetradecyloxybenzylidene-p'-amino-2-methylbutyl-α-cyanocinnamate
(TDOBAMBCC)

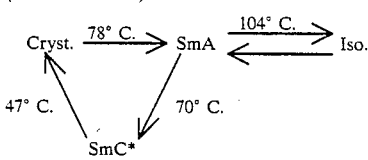

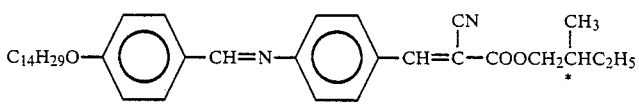

p-octyloxybenzylidene-p'-amino-2-methylbutyl-α-chlorocinnamate
(OOBAMBCC)

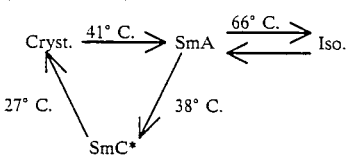

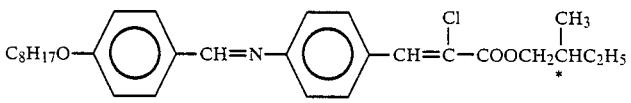

p-octyloxybenzylidene-p'-amino-2-methylbutyl-α-methylcinnamate

Cryst. $\underset{\longleftarrow}{\overset{49° C.}{\longrightarrow}}$ SmC* $\underset{\longleftarrow}{\overset{58° C.}{\longrightarrow}}$ SmA $\underset{\longleftarrow}{\overset{94° C.}{\longrightarrow}}$ Iso.

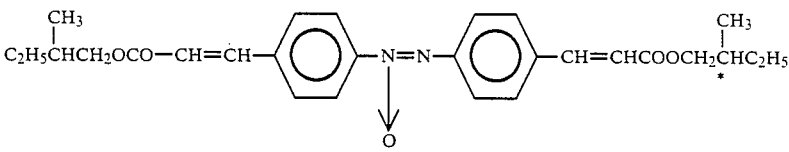

4,4'-azoxycinnamic acid-bis(2-methylbutyl)ester

Cryst. $\underset{\longleftarrow}{\overset{121° C.}{\longrightarrow}}$ SmC* $\underset{\longleftarrow}{\overset{134° C.}{\longrightarrow}}$ SmC $\underset{\longleftarrow}{\overset{168° C.}{\longrightarrow}}$ Iso.

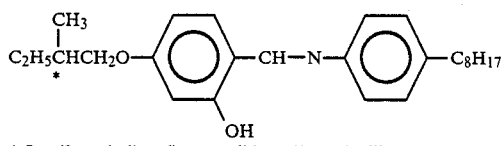

4-O—(2-methylbutyl)resorcylidene-4'-octylaniline

Cryst. ⇌ 28° C. SmC* ⇌ 55° C. SmA ⇌ 62° C. Iso.

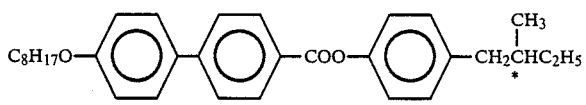

4-(2'-methylbutyl)phenyl-4'-octyloxybiphenyl-4-carboxylate

Cryst. ⇌ 78° C. Sm3 ⇌ 80° C. SmC* ⇌ 128.3° C. SmA ⇌ 171.0° C. Ch. ⇌ 174.2° C. Iso.

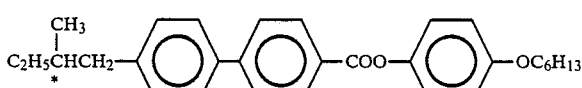

4-hexyloxyphenyl-4-(2''-methylbutyl)biphenyl-4'-carboxylate

Cryst. ⇌ 68.8° C. SmC* ⇌ 80.2° C. Ch. ⇌ 163.5° C. Iso.

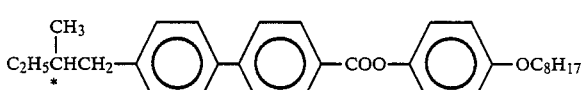

4-octyloxyphenyl-4-(2''-methylbutyl)biphenyl-4'-carboxylate

Cryst. ⇌ 76° C. SmC* ⇌ 88.6° C. Ch. ⇌ 155.4° C. Iso.

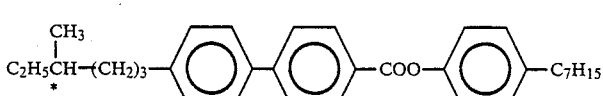

4-heptylphenyl-4-(4''-methylhexyl)biphenyl-4'-carboxylate

Cryst. ⇌ 91.5° C. SmC* ⇌ 93° C. SmA ⇌ 112° C. Ch. ⇌ 131° C. Iso.

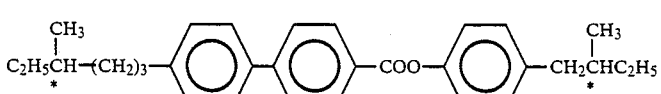

4-(2''-methylbutyl)phenyl-4-(4''-methylhexyl)biphenyl-4'-carboxylate

Cryst. →83.4° C. Ch. →114° C. Iso.
↓ 81.0° C.
SmC* ⇌ 74.3° C. SmA

The mesomorphic compound represented by the formula (I) may also be mixed with a smectic liquid crystal such as those of the formulas <14>–<18> below which per se are not chiral to provide a composition which may be used as a ferroelectric liquid crystal. In this case, the mesomorphic compound represented by the formula (I) may preferably be used in an amount of 0.1–99 wt. %, particularly 1–90 wt. %. The resultant composition may be provided with an increased spontaneous polarization corresponding to the content of the mesomorphic compound according to the present invention.

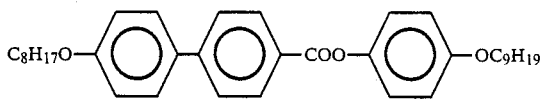

(4-nonyloxyphenyl)-4'-octyloxybiphenyl-4-carboxylate

Cryst. $\underset{74°\text{C.}}{\overset{107°\text{C.}}{\rightleftarrows}}$ SmB $\overset{117°\text{C.}}{\rightleftarrows}$ SmC $\overset{160°\text{C.}}{\rightleftarrows}$ SmA $\overset{195°\text{C.}}{\rightleftarrows}$ Iso.

<15>

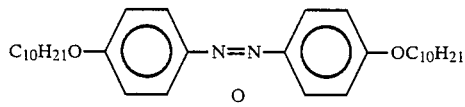

4,4'-decyloxyazoxybenzene

Cryst. $\overset{77°\text{C.}}{\rightarrow}$ SmC $\overset{120°\text{C.}}{\rightleftarrows}$ N $\overset{123°\text{C.}}{\rightleftarrows}$ Iso.

<16>

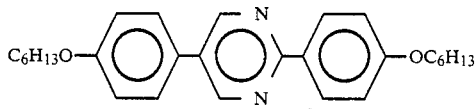

2-(4'-hexyloxyphenyl)-5-(4-hexyloxyphenyl)-pyrimidine

Cryst. $\overset{120°\text{C.}}{\rightarrow}$ SmC $\overset{189°\text{C.}}{\rightleftarrows}$ SmA $\overset{216°\text{C.}}{\rightleftarrows}$ Iso.

<17>

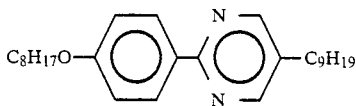

2-(4'-octyloxyphenyl)-5-nonylpyrimidine

Cryst. $\overset{33°\text{C.}}{\rightarrow}$ SmC $\overset{60°\text{C.}}{\rightleftarrows}$ SmA $\overset{75°\text{C.}}{\rightleftarrows}$ Iso.

<18>

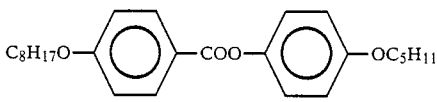

4'-pentyloxyphenyl-4-octylazoxybenzoate

Cryst. $\overset{58°\text{C.}}{\rightarrow}$ SmC $\overset{64°\text{C.}}{\rightarrow}$ SmA $\overset{66°\text{C.}}{\rightarrow}$ N $\overset{85°\text{C.}}{\rightarrow}$ Iso.

Herein, the symbols respectively denote the following phase:
  Cryst.: crystal phase
  SmA: smectic A phase
  SmB: smectic B phase
  SmC: smectic C phase
  N: nematic phase
  Iso.: isotropic phase Further, the mesomorphic compound represented by the formula (I) is effective to prevent occurrence of reverse domain in a TN-type cell when it is added to a nematic liquid crystal. In this case, the mesomorphic compound represented by the formula (I) may preferably be used in an amount of 0.01–50 wt. % of the resultant liquid crystal composition.

Further, it is possible to add the mesomorphic compound according to the present invention to a nematic liquid crystal or a chiral nematic liquid crystal to provide a chiral nematic liquid crystal composition which may be effectively used in a phase-transition type liquid crystal device or a White-Taylor type guest host liquid crystal device. In this case, the mesomorphic compound represented by the formula (I) may preferably be used in an amount of 0.01–80 wt. % of the resultant liquid crystal composition.

Hereinbelow, the present invention will be explained in more detail with reference to the Examples.

EXAMPLE 1

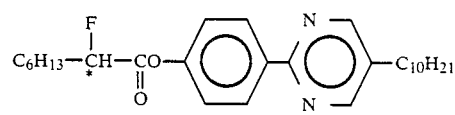

5-n-decyl-2-[4-(2-fluoroocatanoyloxy)phenyl]-pyrimidine represented by the above formula was prepared along the following scheme;

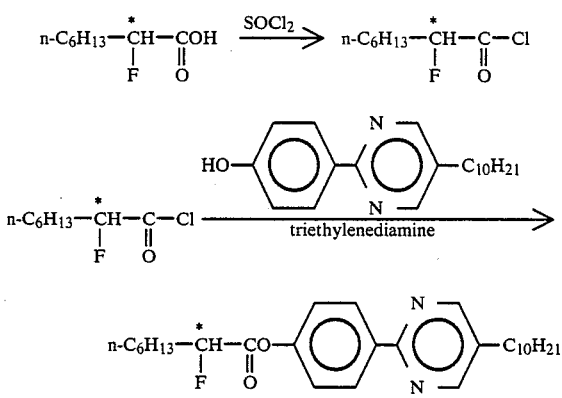

More specifically, 0.24 mg (1.5 mmol) of 2-fluorooctanoic acid was added to 2 ml of thionyl chloride and the mixture was refluxed at 90° C. for 2 hours. Then, the excess of thionyl chloride was distilled off, and a preliminarily prepared solution of 0.34 g (3.0 mmol) of triethylenediamine and 0.47 g (1.5 mmol) of 5-n-decyl-2-(p-hydroxyphenyl)pyrimidine in 5 ml of dry benzene was quickly added thereto, followed by 2 hours of stirring at 50° C. Thereafter, 0.06 g (1.5 mmol) of sodium hydride (60%) was added, and the mixture was further refluxed for 2 hours at 90° C. After the reaction, 2N-hydrochloric acid was added to the system, which was then subjected to extraction with benzene. The extract was dried, subjected to distillation of the solvent and purified by column chromatography with benzene to obtain 0.44 g (0.96 mmol) of 5-n-decyl-2-[4-(2-fluorooctanoyloxy)phenyl]pyrimidine. Yield: 64%

$[\alpha]_D^{26.0}$ +3.14° c=1.018, $CH_2Cl_2$)

$[\alpha]_{435}^{24.8}$ +12.6° (c=1.018, $CH_2Cl_2$).

wherein c denotes a concentration expressed in terms of g/c.c.

EXAMPLES 2–7

Mesomorphic compounds of Examples 2–7 shown in the following Table 1 were prepared similarly as in Example 1.

The optical rotations and phase transition temperatures of the thus prepared mesomorphic compounds of Examples 1–7 are also shown in the following Table 1. In the table, Cryst. denotes a crystalline state; Iso., isotropic liquid; Ch., cholesteric phase; SmA, smectic A phase; SmC*, chiral smectic C phase; $S_C^*$, a chiral smectic phase (un-identified); and $S_3$, a smectic phase (un-identified).

TABLE 1

$$R_1-\underset{*}{\overset{F}{\underset{|}{CH}}}-\underset{\underset{O}{\|}}{C}-O-\text{[structure]}-R_2$$

| Example | $R_1$ | $R_2$ | Optical rotation ($[\alpha]_D$) | Phase transition temperature (°C.) |
|---|---|---|---|---|
| 1 | n-$C_6H_{13}$— | —$C_{10}H_{21}$ | +3.14° (C26° C.) c = 1.018, $CH_2Cl_2$ | Cryst. $\xrightarrow{57}$ Iso. ↘45 ↖27 $S_3 \xleftarrow{32}$ $S_C^*$ |
| 2 | n-$C_8H_{17}$— | —$C_8H_{17}$ | +2.55° (17.6° C.) c = 0.71, $CH_2Cl_2$ | Cryst. $\underset{40}{\overset{55}{\rightleftarrows}}$ Iso |
| 3 | n-$C_8H_{17}$— | —$C_9H_{19}$ | +2.54° (27.6° C.) c = 9.71, $CH_2Cl_2$ | Cryst. $\xrightarrow{64}$ Iso ↘46 ↖42 $S_A$ |
| 4 | n-$C_8H_{17}$— | —$C_{10}H_{21}$ | +2.02° (27.2° C.) c = 0.69, $CH_2Cl_2$ | Cryst. $\xrightarrow{59}$ Iso. ↘48 ↖33 $S_C^* \xleftarrow{43} S_A \xleftarrow{46}$ Ch. |
| 5 | n-$C_6H_{13}$— | —$C_8H_{17}$ | +4.6° (24.0° C.) c = 0.914, $CH_2Cl_2$ | Cryst. $\xrightarrow{56}$ Iso. ↘38 ↖30 $S_A$ |
| 6 | n-$C_6H_{13}$— | —$C_9H_{19}$ | +3.29°(24.8° C.) c = 0.98, $CH_2Cl_2$ | Cryst. $\xrightarrow{53}$ Iso. ↘46 ↖33 $S_A$ |

TABLE 1-continued $$R_1-\overset{*}{C}H-\underset{F}{\overset{|}{C}}-\underset{O}{\overset{||}{C}}-O-\text{Ph}-\text{Pyrimidine}-R_2$$

| Example | $R_1$ | $R_2$ | Optical rotation ($[\alpha]_D$) | Phase transition temperature (°C.) |
|---|---|---|---|---|
| 7 | n-$C_6H_{13}$— | —$C_{12}H_{25}$ | +3.24° (18.4°C.) c = 0.93, $CH_2Cl_2$ | Cryst. ⇌(62) Iso. ⇌(52) Sc* ⇌(47) Cryst. |

EXAMPLE 8

A liquid crystal composition A shown below was prepared by using the mesomorphic compound of Example 1 above. For the purpose of comparison, a liquid crystal composition B shown below was prepared similarly but without using the mesomorphic compound of Example 1. The phase transition temperatures and spontaneous polarizations of the liquid crystal compositions A and B are also shown below.

Separately, two 0.7 mm-thick glass plates were provided and respectively coated with an ITO film to form an electrode for voltage application, which was further coated with an insulating layer of vapordeposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 minutes.

<Liquid Crystal Composition A> n-$C_8H_{17}O$—Ph—COO—Ph—O$CH_2\overset{*}{C}H(CH_3)C_2H_5$   72.0 wt. % n-$C_8H_{17}O$—Ph—OCO—Ph—Ph—$CH_2\overset{*}{C}H(CH_3)C_2H_5$   18.0 wt. % n-$C_{10}H_{21}$—Pyrimidine—Ph—O$\underset{O}{\overset{||}{C}}$—$\overset{*}{C}H(F)$—$C_6H_{13}$   10.0 wt. %

Phase transition temperature (°C.)

Cryst. ⇌(17/10) Sc* ⇌(45/44) $S_A$ ⇌(61/60) Ch. ⇌(70/70) Iso

<Liquid Crystal Composition B> n-$C_8H_{17}O$—Ph—COO—Ph—O$CH_2\overset{*}{C}H(CH_3)C_2H_5$   80.0 wt. % n-$C_8H_{17}O$—Ph—OCO—Ph—Ph—$CH_2\overset{*}{C}H(CH_3)C_2H_5$   20.0 wt. %

Phase transition temperature (°C.)

Cryst. ⇌(20/18) Sc* ⇌(53/52) $S_A$ ⇌(65/64) Ch. ⇌(76/75) Iso.

| Spontaneous polarization (nC/cm²) | | |
|---|---|---|
| Temp. (°C.) | L. C. Composition A. | L. C. Composition B |
| 40 | 4.3 | 1.2 |
| 30 | 7.7 | 20 |

Further, each glass plate provided with an ITO film and treated in the above described manner was coated with a 2%-solution of polyimide resin precursor (SP-510, available from Toray K.K.) in dimethylacetoamide by a spinner coated rotating at 2000 rpm for 15 seconds. Thereafter, the coating film was subjected to heat curing at 300° C. for 60 min. to obtain about 700 Å-thick film. The coating film was rubbed with acetate fiber-planted cloth. The thus treated two glass plates were washed with isopropyl alcohol. After alumina beads with an average particle size of 1.5 μm were dispersed on one of the glass plates, the two glass plates were applied to each other with a bonding sealing agent (Lixon Bond available from Chisso K.K.) so that their rubbed directions were parallel to each other and heated at 100° C. for 60 minutes to form a blank cell. The cell gap was found to be about 2 μm as measured by a Berek compensator.

Two cells thus prepared were filled under vacuum with the above-prepared liquid crystal compositions A and B, respectively, heated into an isotropic phase, and gradually cooled at a rate of 0.5° C./hr to obtain two ferroelectric liquid crystal devices.

Then, the optical response time (time from voltage application until the transmittance change reaches 90% of the maximum) was measured for each device under the application of a peak-to-peak voltage of 30V in combination with right-angle cross-nicol polarizers.

| Temp. (°C.) | Response time (msec) | |
| --- | --- | --- |
| | L.C. Composition A | L.C. Composition B |
| 40 | 0.06 | 0.55 |
| 30 | 0.13 | 0.93 |

EXAMPLE 9

Optically active 2-fluorobutanoic acid-p-(5-dodecyl-2-pyrimidyl)phenyl-ester was prepared according to the following reaction scheme:

cyl-2-pyrimidyl)phenyl-ester was obtained. The yield was 27%.

$[\alpha]_D^{27} -1.22$ (c=0.82, dichloromethane)

example 10

Optically active 2-fluoropropanoic acid-p-(5-decyl-2-pyrimidyl)phenyl-ester was prepared along the following scheme.

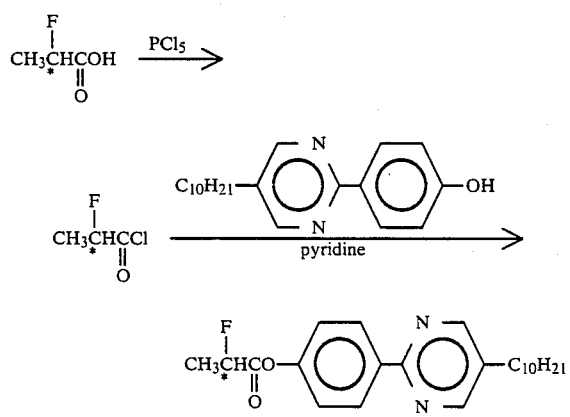

Thus, 1.6 g (174 mmol) of 2-fluoropropanoic acid was dissolved in 10 ml of benzene, to which 177 mmol of phosphorus pentoxide was added little by little in 20 minutes under stirring. Then, the mixture was raised in temperature and refluxed under heating for four hours to obtain an acid chloride.

5.4 g (173 mmol) of p-(5-decyl-2-pyrimidyl)-phenol and 1.4 g (177 mmol) of pyridine were dissolved in 30 ml of benzene, and a benzene solution of the above 2-fluoropropanoic acid chloride was added dropswise thereto at 5° C. in 15 minutes. Then, the mixture was stirred overnight at room temperature, and after the completion of the reaction, the reaction solution was poured into ice water. Then, the system was acidified

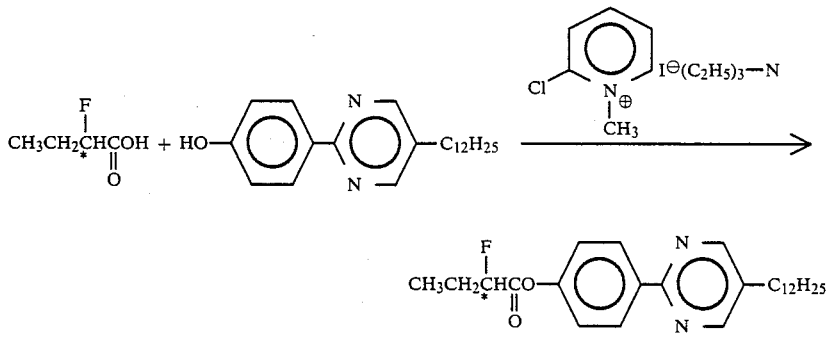

More specifically, into a solution of 0.34 g (1.0 mmol) of p-(5-dodecyl-2-pyrimidyl)phenol and 0.22 g (2.0 mmol) of triethylamine in dry dichloromethane, a solution of 0.11 g (1.0 mmol) of (3□)-2-fluorobutanoic acid in dry dichloromethane and 0.31 g (1.2 mmol) of 2-chloro-1-methylpyridinium iodide were added, and the resultant mixture was refluxed under heating for 1 hour in nitrogen atmosphere. After the reaction was completed, dichloroethane was distilled off, and the product was purified by column chromatography (eluent: dichloromethane) and recrystallization from hexane. As a result, 0.11 g (0.27 mmol) of 2-fluoro-butanoic acid-p(5-dodewith the addition of 6N-HCl and subjected to extraction with benzene. The extract benzene solution was washed with water and saline water, dried with anhydrous magnesium sulfate, and the solvent was distilled to leave 3.2 g of a crude product. The product was purified by column chromatography (eluent: hexane/acetone=10/1) to obtain 330 mg of 2-fluoropropanoic acid-p-(5-decyl-2-pyrimidyl)phenyl-ester. Yield: 5.0%.

EXAMPLES 11-13

Example 9 was repeated by using p-(5-octyl-2-pyrimidyl)phenol, (5-nonyl-2-pyrimidyl)phenol and p-(5-decyl-2-pyrimidyl)phenyl, respectively, in place of the p-(5-dodecyl-2-pyrimidyl)phenol to obtain the following compounds:

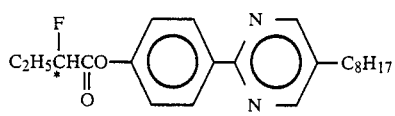

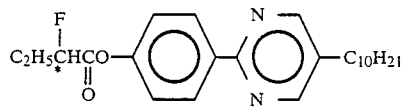

The phase transition temperature and optical rotation data for these compounds are shown in the following Table 2 together with those for the compounds of Examples 9 and 10. The symbols used in Table 2 have the same meanings in Table 1.

TABLE 2

| Example | $R_1$ | $R_2$ | Optical rotation ($[\alpha]_D$) | Phase transition temperature (°C.) |
|---|---|---|---|---|
| 9 | $C_2H_5-$ | $-C_{12}H_{25}$ | $-1.22°$ (27° C.) (c = 0.82, $CH_2Cl_2$) | Cryst. ⇌(69/50) Iso., ↘59 SmA |
| 10 | $CH_3-$ | $-C_{10}H_{21}$ | — | Cryst. ⇌(71/53) Iso. |
| 11 | $C_2H_5-$ | $-C_8H_{17}$ | — | Cryst. ⇌(60/48) Iso. |
| 12 | $C_2H_5-$ | $-C_9H_{19}$ | $+1.78°$ (32° C.) (c = 0.79, $Et_2O$) | Cryst. ⇌(70/55) Iso., ↘58 $S_3$ |
| 13 | $C_2H_5-$ | $-C_{10}H_{21}$ | $+2.86°$ (32° C.) (c = 0.98, $CH_2Cl_2$) | Cryst. ⇌(69/57) Iso. |

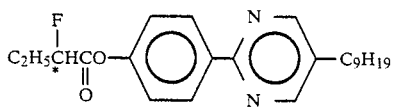

EXAMPLE 14

A liquid crystal Composition C shown below was prepared by using the mesomorphic compound of Example 13 in Table 2. The composition, phase transition temperature and optical rotation are shown below in parallel with those of the Composition A in Example 8 which was different from the Composition C only in that the mesomorphic compound of Example 1 having a longer carbon chain in its optically active group was used instead of the Composition C.

<Liquid Crystal Composition>

$C_8H_{17}O-\bigcirc-CO-O-\bigcirc-OCH_2\overset{*}{C}HC_2H_5$ (with $CH_3$)  72.0 wt. %

$C_8H_{17}O-\bigcirc-OC(=O)-\bigcirc-\bigcirc-CH_2\overset{*}{C}HC_2H_3$ (with $CH_3$)  18.0 wt. %

$C_{10}H_{21}-\bigcirc(N,N)-\bigcirc-OC(=O)\overset{*}{C}HC_2H_5$ (with F)  10.0 wt. %

Phase transition temperature (°C.)

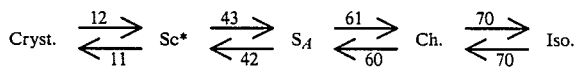

<Liquid Crystal Composition A>

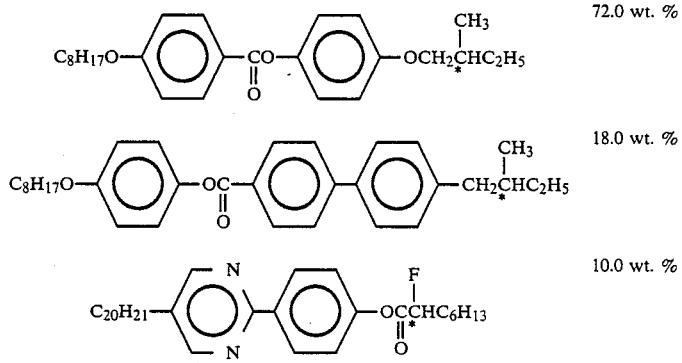

72.0 wt. %

18.0 wt. %

10.0 wt. %

Phase transition temperature (°C.)

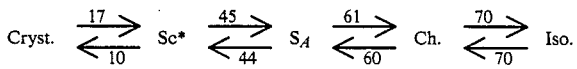

| Temp. (°C.) | Spontaneous polarization (nC/cm²) | |
|---|---|---|
| | L. C. Composition C | L. C. Composition A |
| 40 | 3.6 | 4.3 |
| 30 | 8.1 | 7.7 |

A ferroelectric liquid crystal device was prepared in the same manner as in Example 8 by using the above Liquid Crystal Composition C.

The optical response time of the ferroelectric liquid crystal device thus produced was measured similarly and is shown below together with that of the device using the Composition A.

| Temp. (°C.) | Optical response time (msec) | |
|---|---|---|
| | L.C. Composition C | L.C. Composition A |
| 40 | 0.03 | 0.06 |
| 30 | 0.08 | 0.13 |

The above results show that the liquid crystal Compositions C and A did not show substantial difference with respect to phase transition temperature or spontaneous polarization, but the Composition C containing a mesomorphic compound having a shorter carbon chain in the optically active group showed a higher response speed.

EXAMPLE 15

Two glass plates each provided with an ITO transparent electrode film were coated with a film of a polyimide resin precursor (SP 510, available from Toray K.K.) by spinner coating, followed by heating at 300° C. for 60 minutes to form polyimide films. The polyimide films were further treated by rubbing, and the two glass plates thus treated were applied to each other to form a blank cell having a cell gap of 8 μm. The cell was filled with a biphenyl-type nematic liquid crystal composition (Lixon GR-63, available from Chisso K. K.) to form a TN-type cell. The cell was then observed through a polarizing microscope, whereby a reverse domain (fringe pattern) was observed.

A TN-type cell was prepared similarly except for using a liquid crystal composition obtained by adding 1 wt. part of the mesomorphic compound of Example 2 above to 99 wt. parts of the above-mentioned Lixon GR-63. As a result of observation through a polarizing microscope, no reverse domain was observed but a uniform nematic phase was found to be formed. Thus, it was found that the mesomorphic compound according to the present invention was effective in preventing occurrence of reverse domain.

As described above, according to the present invention, there is provided a mesomorphic compound represented by the above-mentioned formula (I) and having a fluorine atom providing a larger dipole moment directly bonded to its asymmetric carbon atom. Further, by adding at least one species of the mesomorphic compound as a constituent, it is possible to provide a TN-type liquid crystal composition with little occurrence of reverse domain, or a chiral nematic liquid crystal composition or a chiral smectic liquid crystal composition with an improved electric field-responsive characteristic. It is further possible to control the liquid crystal state of the resultant liquid crystal composition.

What is claimed is:

1. An optically active compound represented by the following formula (I):

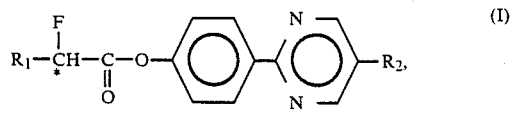

wherein $R_1$ and $R_2$ are respectively an alkyl group having 1 to 16 carbon atoms, and C* denotes an asymmetric carbon atom.

2. A compound according to claim 1, which is

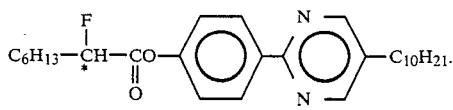

3. A compound according to claim 1, which is

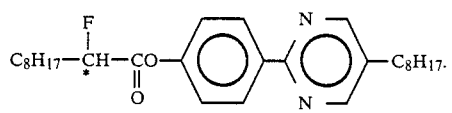

4. A compound according to claim 1, which is

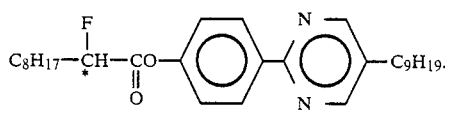

5. A compound according to claim 1, which is

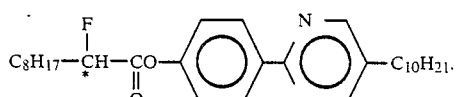

6. A compound according to claim 1, which is

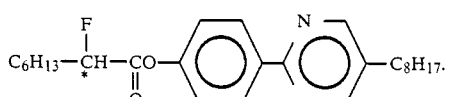

7. A compound according to claim 1, which is

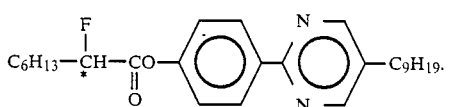

8. A compound according to claim 1, which is

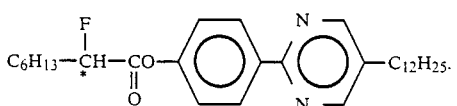

9. A compound according to claim 1, which is

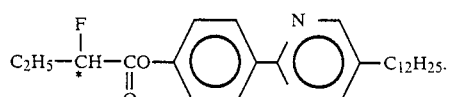

10. A compound according to claim 1, which is

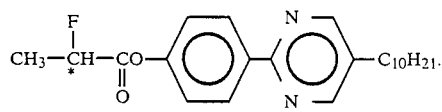

11. A compound according to claim 1, which is

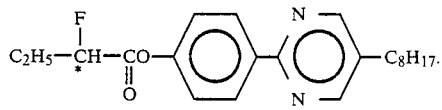

12. A compound according to claim 1, which is

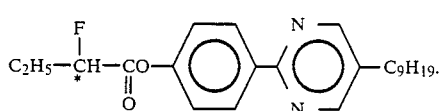

13. A compound according to claim 1, which is

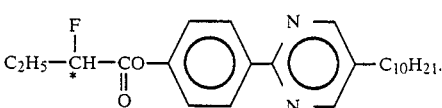

14. A liquid crystal composition comprising at least two compounds and containing at least one compound represented by the following formula (I):

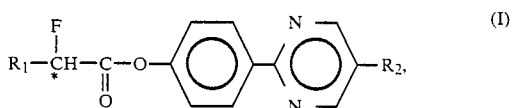

wherein $R_1$ and $R_2$ are respectively an alkyl group having 1 to 16 carbon atoms and C* denotes an asymmetric carbon atom.

15. A liquid crystal composition according to claim 14, which contains a ferroelectric liquid crystal in addition to said at least one compound.

16. A liquid crystal composition according to claim 14, which contains a non-chiral smectic liquid crystal in addition to said at least one compound.

17. A liquid crystal composition according to claim 14, which contains a nematic liquid crystal in addition to said at least one compound.

18. A liquid crystal device, which comprises a pair of oppositely spaced electrodes and a liquid crystal composition disposed between the oppositely spaced electrodes; said liquid crystal composition comprising at least two compounds and containing at least one compound represented by the following formula (I):

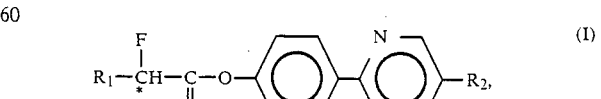

wherein $R_1$ and $R_2$ are respectively an alkyl group having 1 to 16 carbon atoms, and C* denotes an asymmetric carbon atom.

19. A liquid crystal device according to claim 18, wherein said liquid crystal composition contains a ferroelectric liquid crystal in addition to said at least one compound.

20. A liquid crystal device according to claim 18, wherein said liquid crystal composition contains a non-chiral smectic liquid crystal in addition to said at least one compound.

21. A liquid crystal device according to claim 18, wherein said liquid crystal composition contains a nematic liquid crystal in addition to said at least one compound.

* * * * *

UNITED STATES PATENT AND TRADEMARK OFFICE
CERTIFICATE OF CORRECTION

PATENT NO. 4,904,410

DATED : February 27, 1990

INVENTOR(S) : HIROYUKI NOHIRA, ET AL.

It is certified that error appears in the above-identified patent and that said Letters Patent is hereby corrected as shown below:

Title page:

IN [56] REFERENCES CITED

FOREIGN PATENT DOCUMENTS, "3515273 11/86" should read --3515373 11/86--.

COLUMN 1

Line 20, "phenomenon" should be deleted.
    Line 57, "is" should read --in--.
    Line 64, "system" should read --systems--.

COLUMN 2

Line 26, "seldome" should read --rare--.
    Line 36, "fieldresponsive" should read --field-responsive--.
    Line 47, "therefore" should read --therefor--.

COLUMN 6

Line 47, "represent" should read --represented--.

COLUMN 11

Formula <15>, "N=N ... O" should read --N=N ... O--.
    Line 50, "phase:" should read --phases:--.

UNITED STATES PATENT AND TRADEMARK OFFICE
CERTIFICATE OF CORRECTION

PATENT NO. : 4,904,410

DATED : February 27, 1990

INVENTOR(S) : HIROYUKI NOHIRA, ET AL.

It is certified that error appears in the above-identified patent and that said Letters Patent is hereby corrected as shown below:

COLUMN 14

Line 10, "$CH_2Cl_2$)." should read --$CH_2Cl_2$),--.
TABLE 1, In Example 3, "c = 9.71," should read --c = 0.71,--.

COLUMN 15

Line 65, "L.C. Composition B.
             1.2
             20 "            should read --L.C. Composition B.
       1.2
       2.0 --.

COLUMN 16

Line 19, "vapordeposited $SiO_2$" should read --vapor-deposited $SiO_2$--.
Line 23, "second" should read --seconds--.

COLUMN 18

Line 5, "example 10" should read --EXAMPLE 10--.

UNITED STATES PATENT AND TRADEMARK OFFICE
CERTIFICATE OF CORRECTION

PATENT NO. : 4,904,410

DATED : February 27, 1990

INVENTOR(S) : HIROYUKI NOHIRA, ET AL.

It is certified that error appears in the above-identified patent and that said Letters Patent is hereby corrected as shown below:

COLUMN 20

Line 11, "meanings in" should read --meanings as in--.

Line 54, "<Liquid Crystal Composition>" should read --<Liquid Crystal Composition C>--.

COLUMN 21

Line 21, "$C_{20}H_{21}-$" should read --$C_{10}H_{21}-$--.

Signed and Sealed this

Seventeenth Day of September, 1991

Attest:

HARRY F. MANBECK, JR.

Attesting Officer

Commissioner of Patents and Trademarks